US010441175B2

(12) United States Patent
Xi et al.

(10) Patent No.: US 10,441,175 B2
(45) Date of Patent: Oct. 15, 2019

(54) TOOTHBRUSH WITH REMOVABLE SMART DEVICE

(71) Applicant: Colgate-Palmolive Company, New York, NY (US)

(72) Inventors: Wen Jin Xi, Shanghai (CN); Guang Sheng Guo, Yangzhou (CN)

(73) Assignee: Colgate-Palmolive Company, New York, NY (US)

( * ) Notice: Subject to any disclaimer, the term of this patent is extended or adjusted under 35 U.S.C. 154(b) by 313 days.

(21) Appl. No.: 15/391,372

(22) Filed: Dec. 27, 2016

(65) Prior Publication Data

US 2017/0188836 A1 Jul. 6, 2017

(30) Foreign Application Priority Data

Dec. 31, 2015 (CN) .......................... 2015 1 1036171

(51) Int. Cl.
| | | |
|---|---|---|
| *A61B 5/00* | (2006.01) | |
| *A61B 5/02* | (2006.01) | |
| *A46B 15/00* | (2006.01) | |
| *A46B 5/02* | (2006.01) | |
| *A46B 9/04* | (2006.01) | |
| *A61B 5/103* | (2006.01) | |
| *A61B 5/08* | (2006.01) | |
| *A61B 1/24* | (2006.01) | |

(52) U.S. Cl.
CPC .............. *A61B 5/0088* (2013.01); *A46B 5/02* (2013.01); *A46B 9/04* (2013.01); *A46B 15/0004* (2013.01); *A46B 15/0034* (2013.01); *A46B 15/0036* (2013.01); *A46B 15/0055* (2013.01); *A61B 1/24* (2013.01); *A61B 5/0022* (2013.01); *A61B 5/082* (2013.01); *A61B 5/1032* (2013.01); *A61B 5/742* (2013.01); *A46B 2200/1066* (2013.01)

(58) Field of Classification Search
CPC ....... A61B 5/0088; A61B 1/24; A61B 5/0022; A61B 5/082; A61B 5/1032; A61B 5/742; A46B 5/02; A46B 9/04; A46B 15/0004; A46B 15/0034; A46B 15/0036; A46B 15/0055
See application file for complete search history.

(56) References Cited

U.S. PATENT DOCUMENTS

| | | |
|---|---|---|
| 7,748,069 B2 | 7/2010 | Dawley |
| 8,337,213 B2 | 12/2012 | Puurunen |
| 8,585,411 B2 | 11/2013 | Puurunen et al. |

(Continued)

FOREIGN PATENT DOCUMENTS

| | | |
|---|---|---|
| CN | 101606783 A | 12/2009 |
| CN | 203913858 U | 3/2014 |

(Continued)

OTHER PUBLICATIONS

International Search Report and the Written Opinion issued in International Application PCT/US2016/068700 dated Mar. 13, 2017.

*Primary Examiner* — Shay Karls

(57) ABSTRACT

In some embodiments, an oral care system includes a toothbrush and a smart device removably retained in the toothbrush and having a plurality of sensors for sensing conditions of the oral cavity. The sensors may include sensors that obtain information while the smart device is retained in the toothbrush and sensors that obtain information while the smart device is separated from the toothbrush.

20 Claims, 8 Drawing Sheets

(56) References Cited

U.S. PATENT DOCUMENTS

| | | |
|---|---|---|
| 9,105,197 B2 | 8/2015 | Meriheinae et al. |
| 9,552,743 B2 | 1/2017 | Meriheinae et al. |
| 9,936,795 B2 | 4/2018 | Moskovich et al. |
| 2008/0102953 A1 | 5/2008 | Schultz |
| 2011/0275424 A1 | 11/2011 | Schmid et al. |
| 2012/0310593 A1 | 12/2012 | Bates et al. |
| 2014/0272768 A1* | 9/2014 | Curry .............. A61B 5/0088 433/27 |
| 2015/0205279 A1 | 7/2015 | Simeth |
| 2015/0230594 A1* | 8/2015 | De Vries .......... A46B 15/0014 15/22.1 |

FOREIGN PATENT DOCUMENTS

| | | | |
|---|---|---|---|
| CN | 104257434 A | 1/2015 | |
| CN | 104257435 | 1/2015 | |
| CN | 104305711 A | 1/2015 | |
| CN | 104783487 A | 7/2015 | |
| EP | 2896319 A2 * | 7/2015 | ............ A45D 27/22 |
| EP | 2603112 | 6/2018 | |
| EP | 2326208 | 1/2019 | |
| KR | 2009 0125455 | 12/2009 | |
| WO | WO 2013/001462 | 1/2013 | |
| WO | WO2015073062 A1 | 5/2015 | |
| WO | 2015/094230 | 6/2015 | |

\* cited by examiner

TOOTHBRUSH WITH REMOVABLE SMART DEVICE

BACKGROUND

Myriad implements and devices for maintaining oral health are known. For example, toothbrushes, floss, dentifrices, applicators, and the like all are known to provide different benefits in the oral cavity. Moreover, some devices and methods exist to monitor oral health. However, whether a user is properly using the implements and devices and, more generally, the user's overall oral health, are often unknown to a user. While a person may visit the dentist every six-months, it would be beneficial for a user to more regularly be provided with diagnoses and information relating to their oral health.

Thus, there is a need in the art for a toothbrush that integrates oral health diagnostics with oral health cleaning. This disclosure is directed at overcoming one or more problems set forth above and/or other problems of the prior art.

BRIEF SUMMARY

This application describes improved oral care implements that incorporate a smart device capable of monitoring one or more aspects of oral health. In some embodiments, the implement may include a toothbrush, and a handle of the toothbrush may include a receptacle for removably retaining a smart device. The smart device may include sensors for sensing different parameters, including a first oral health parameter measured while the smart device is retained in the handle of the toothbrush and a second oral health parameter measured while the smart device is separate from the toothbrush.

Also described herein are methods of monitoring oral health conditions using a toothbrush having a smart device releasably retained in its handle. In one example method, position and/or movement of the toothbrush are sensed by first sensors in the smart device while the smart device is retained in the handle of the toothbrush and an oral health condition is sensed by second sensors in the smart device while the smart device is removed from the handle of the toothbrush. Information relating to the position and/or movement of the toothbrush sensed by the first sensors and information relating to the oral health condition sensed by the second sensors is transmitted from the smart device to a remote device. In some implementations, the remote device may be a personal electronic device, such as a smartphone, and the information relating to the position and/or movement of the toothbrush sensed by the first sensors and/or the information relating to the oral health condition sensed by the second sensors may be displayed on a display of the personal electronic device.

In one example implementation of this disclosure, an oral care system includes a handle extending from a proximal end to a distal end, the handle comprising a sidewall defining a receptacle in the handle and an opening to the receptacle at the proximal end of the handle; a head disposed proximate the distal end of the handle and comprising a tooth cleaning element; and a smart device selectively receivable in the receptacle of the handle and comprising a first sensor for acquiring first oral health data with the smart device in a retained position in the cavity in the handle and a second sensor for acquiring second oral health data with the smart device in a removed position, separate from the handle.

In other aspects, in a system of the preceding paragraph, the first sensor comprises a sensor for determining a position or orientation of the handle or the head with the smart device in the retained position.

In other aspects, in a system of any of the preceding paragraphs, the smart device further comprises a transmitter for transmitting information relating to the position or orientation to a receiver separate from the toothbrush.

In other aspects, in a system of any of the preceding paragraphs, the receiver separate from the toothbrush is associated with an electronic device.

In other aspects, in a system of any of the preceding paragraphs, the electronic device is configured to run an oral health application that displays to a user information about the user's oral health.

In other aspects, in a system of any of the preceding paragraphs, the second sensor comprises an imaging sensor.

In other aspects, in a system of any of the preceding paragraphs, wherein the imaging sensor captures an image of at least a portion of the oral cavity.

In other aspects, in a system of any of the preceding paragraphs, wherein the imaging sensor captures a color image of at least a portion of the oral cavity.

In other aspects, in a system of any of the preceding paragraphs, wherein the smart device further comprises a light emitter for illuminating a portion of the oral cavity.

In other aspects, in a system of any of the preceding paragraphs, the light emitter illuminates bacteria in the oral cavity.

In other aspects, in a system of any of the preceding paragraphs, the second sensor monitors breath freshness.

In other aspects, in a system of any of the preceding paragraphs, the second sensor measures a sulfur level in the breath to determine breath freshness.

In other aspects, in a system of any of the preceding paragraphs, the smart device comprises at least one of a digital gyroscope, a digital accelerometer, and a digital comparator.

In other aspects, in a system of any of the preceding paragraphs, the smart device comprises a transmitter.

In other aspects, in a system of any of the preceding paragraphs, the smart device comprises a power source.

In another aspect of this disclosure, a method of measuring an oral health condition uses a toothbrush. The toothbrush includes a handle having a sidewall defining a receptacle, a head disposed proximate a distal end of the handle and including a tooth cleaning element, and a smart device removably disposed in the receptacle in the handle, the smart device including a first sensor for sensing a position or a movement of the toothbrush and a second sensor for sensing a parameter associated with the oral health condition. The method includes sensing at least one of a position or a movement of the toothbrush, by the first sensor of the smart device, with the smart device retained in the receptacle in the handle; sensing the parameter associated with the oral health condition, by the second sensor of the smart device, with the smart device removed from the receptacle in the handle and placed in a sensing position proximate an oral cavity; and transmitting the position or the movement of the toothbrush or the parameter associated with the oral health condition.

In other aspects, in a method according to the preceding paragraph, the parameter associated with the oral health condition is displayed on an electronic device.

In other aspects, in a method according to either of the preceding two paragraphs, a visual representation containing information relative to the parameter associated with the oral health condition is displayed with the parameter associated with the oral health condition on the electronic device.

In other aspects, in a method according to either of the preceding three paragraphs, the electronic device is a personal electronic device associated with the user.

In other aspects, in a method according to either of the preceding four paragraphs, the transmitting the parameter associated with the oral health condition comprises transmitting the parameter to an oral health care provider.

In other aspects, in a method according to either of the preceding five paragraphs, the parameter associated with the oral health condition is tooth color and further comprising displaying a color image captured by the smart device to the user together with a reference image.

Further areas of applicability of the present disclosure will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the preferred embodiments is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

This disclosure relates generally to an oral care device that incorporates one or more tools for cleaning portions of the oral cavity and one or more tools for sensing conditions of the oral cavity. In some example implementations, this disclosure describes a toothbrush that incorporates tooth cleaning elements, such as bristles or the like, and a smart device having a plurality of sensors for sensing conditions of the oral cavity. The sensors may include sensors that obtain information while a user cleans her teeth. In implementations of this disclosure, that information may be used to display, on a display of a user device, an efficacy of the user's cleaning. The sensors may also include sensors that determine information about aspects of oral health separate from the cleaning. For example, in implementations of this disclosure, the sensors may sense breath freshness, degree of tooth staining, bacteria count on the teeth and gums, and/or gum health. Although certain embodiments and benefits will be described, other implementations, modifications, and/or benefits will be appreciated those having ordinary skill in the art, with the benefit if this disclosure.

Figure 1A:
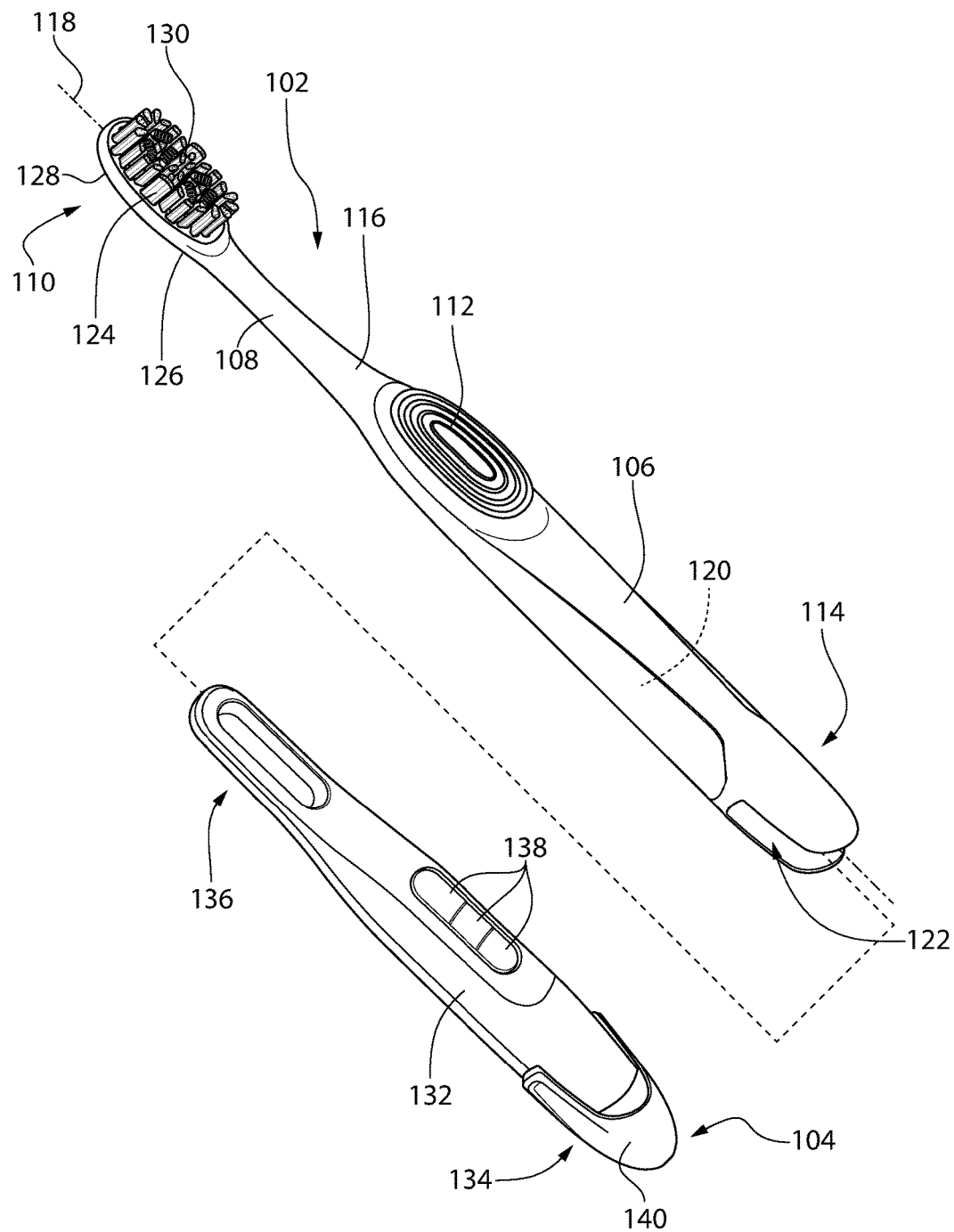
FIG. 1A is an exploded perspective view of an oral care system including a smart device removed from a handle of a toothbrush, according an example implementations of this disclosure.
Figure 1B:
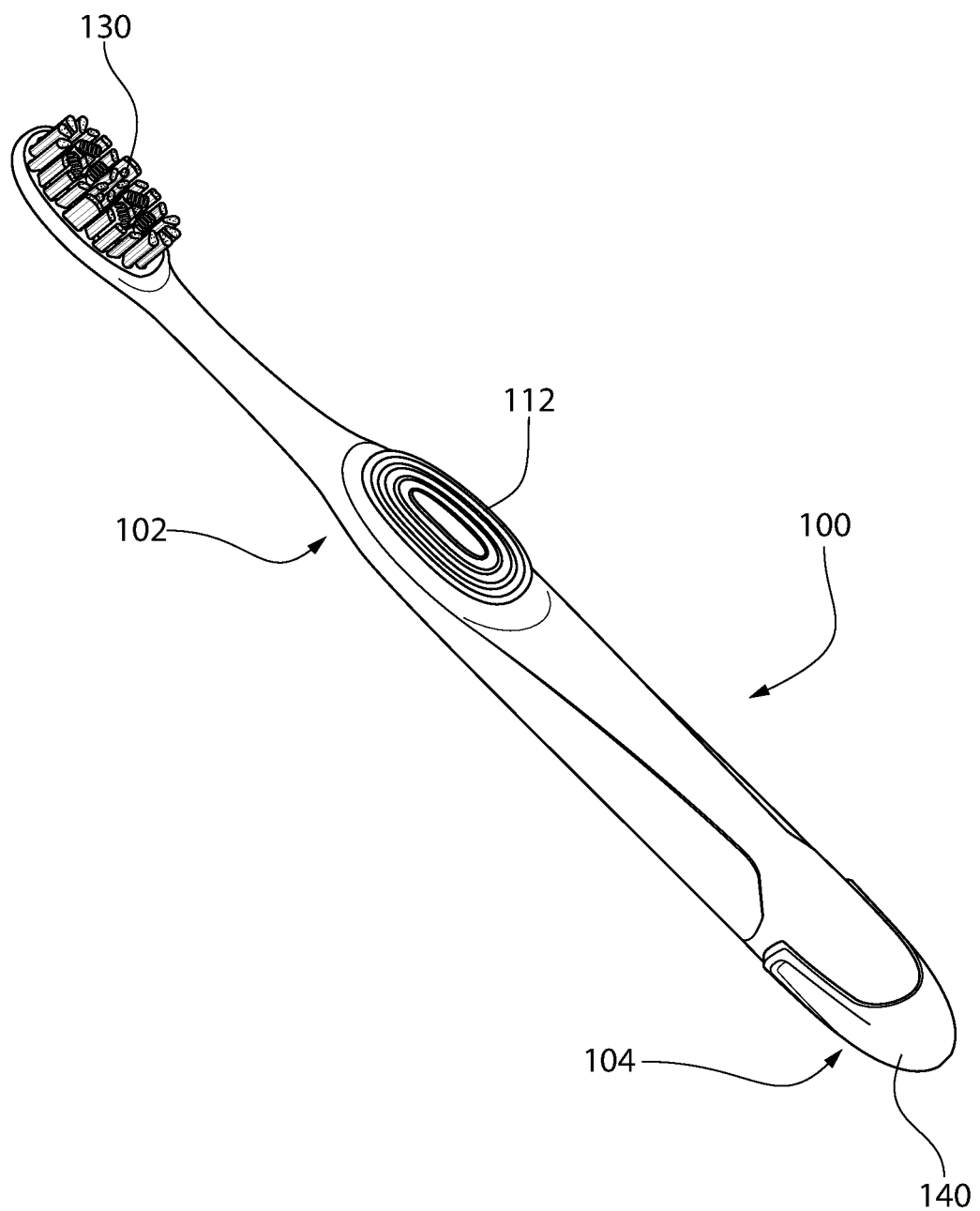
FIG. 1B is a perspective view of the toothbrush of FIG. 1A, with the smart device retained in a the handle of the toothbrush.

FIGS. 1A and 1B generally illustrate an oral care system 100 according to embodiments of this disclosure. In the illustrated embodiment, the oral care system 100 generally takes the form of a modified toothbrush having a removable oral care device disposed at least partially within its handle. Because the smart device is located within the handle of the toothbrush itself, the oral care system 100 is portable for travel, easy to use, and reduces the amount of required storage space. Furthermore, since the toothbrush and smart device are housed together, the user is less likely to misplace the smart device and be more inclined to maintain the oral treatment routine with the smart device since brushing will remind the user to simply detach and apply the contents of the smart device.

The oral care system 100 generally comprises a toothbrush 102 and a smart device 104. While the invention is described herein with respect to the use of a toothbrush as one of the two primary components of the oral care system 100, it is to be understood that other alternate oral care implements can be used within the scope of the invention, including tongue cleaners, tooth polishers and implements having tooth engaging elements specially designed to increase the effect of the active agent in the smart device on the teeth. Moreover, while the toothbrush 102 is preferably a manual toothbrush, the toothbrush may be a powered toothbrush in other embodiments of the invention. As will be described in more detail below, the system 100 can be utilized for a variety of oral health diagnostics using the smart device 104 disposed in the toothbrush 102. Some of the diagnostics may be made while the smart device 104 is attached to the toothbrush 102, while other diagnostics may be made using only the smart device 104, i.e., separate from the toothbrush.

The toothbrush 102 generally comprises a handle portion 106, a neck portion 108 and a head portion 110. The handle 106 provides the user with a mechanism by which he/she can readily grip and manipulate the toothbrush 100. The handle 106 may be formed of many different shapes, sizes, materials and a variety of manufacturing methods that are well-known to those skilled in the art, so long as it can house the smart device 104 therein as described in detail below. If desired, the handle 106 may include a suitable textured grip 112 made of soft elastomeric material. The handle 106 can be a single or multi-part construction. The handle 106 extends from a proximal end 114 to a distal end 116 along a longitudinal axis 118. As will be described in greater detail below with respect to FIG. 2, a cavity 120 is formed within the handle 106. An opening 122 is provided at the proximal end 114 of the handle 106 that provides a passageway into the cavity 120 through which the smart device 104 can be inserted and retracted. In this manner, the cavity 120, as accessed through the opening 122, forms a receptacle for releasably receiving the smart device 104. While the opening 122 is located at the proximal end 114 of the handle in the exemplified embodiment, the opening may be located at other positions on the handle 106 in other embodiments of the invention. For example, the opening 122 may be located on a longitudinal surface of the handle 106 and be elongated to provide sufficient access to the cavity 120.

The handle 106 transitions into the neck 108 at the distal end 116. While the neck 108 generally has a smaller transverse cross-sectional area than the handle 108, the invention is not so limited. The neck 108 is merely the transition region between the handle 106 and the head 110 and can conceptually be considered as a portion of the handle 106. In this manner, the head 110 is connected to the distal end 116 of the handle 106 (via the neck 108).

The head 110 and the handle 108 of the toothbrush 102 are preferably formed as a single unitary structure using a molding, milling, machining or other suitable process. However, in other embodiments, the handle 106 and head 110 may be formed as separate components which are operably connected at a later stage of the manufacturing process by any suitable technique known in the art, including without limitation thermal or ultrasonic welding, a tight-fit assembly, a coupling sleeve, adhesion, or fasteners. Whether the head 110 and handle 106 are of a unitary or multi-piece construction (including connection techniques) is not limiting of the present invention, unless specifically stated. In some embodiment of the invention, the head 110 may be detachable (and replaceable) from the handle 106 using techniques well-known in the art.

The head 110 generally comprises a front surface 124, a rear surface 126 and a peripheral surface 233. The front surface 124 and the rear surface 126 of the head 110 can take on any of a wide variety of shapes and contours, none of which are limiting of the present invention. For example, the front and rear surfaces 124, 126 can be planar, contoured or combinations thereof. Moreover, if desired, the rear surface 126 may also comprise additional structures for oral cleaning or tooth engagement, such as a soft tissue cleaner or a tooth polishing structure. An example of a soft tissue cleaner is an elastomeric pad comprising a plurality of nubs and or ridges. An example of a tooth polishing structure can be an elastomeric element, such as a prophy cup(s) or elastomeric wipers. Furthermore, while the head 110 is normally widened relative to the neck 108 of the handle 106, it could in some constructions simply be a continuous extension or narrowing of the handle 106.

The front surface 124 comprises a collection of oral cleaning elements such as tooth cleaning elements 130 extending therefrom for cleaning and/or polishing contact with an oral surface and/or interdental spaces. While the collection of tooth engaging elements 130 is preferably suited for brushing teeth, the collection of cleaning elements 130 can also be used to polish teeth instead of or in addition to cleaning teeth. As used herein, the term "tooth engaging elements" is used in a generic sense to refer to any structure that can be used to clean, polish or wipe the teeth and/or soft oral tissue (e.g. tongue, cheek, gums, etc.) through relative surface contact. Common examples of "tooth engaging elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material preferably has a hardness property in the range of A8 to A25 Shore hardness. One preferred elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 130 of the present invention can be connected to the head 120 in any manner known in the art. For example, staples/anchors, in-mold tufting (IFT) or anchor free tufting (AFT) could be used to mount the cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

The toothbrush 102 and the smart device 104 are non-unitary, separate structures that are specially designed to be non-fixedly secured together when in an assembled position (referred to herein as a cleaning or retained position) and completely separated from one another when in a disassembled position (referred to herein as a removed or diagnostic position). The toothbrush 102 and the smart device 104 are illustrated in the diagnostic position in FIG. 1A and in the cleaning position in FIG. 1B. The smart device 104 can be moved between the cleaning position (FIG. 1B) in which the smart device is docked in the toothbrush handle portion 106 and the diagnostic position (FIG. 1A) in which the smart device is removed from handle portion 106 by the user as desired, for example, by sliding the smart device in and out of the cavity, via the opening.

In embodiments of this disclosure, the smart device may have diagnostic and/or oral health evaluation functions in both the cleaning position and the diagnostic position. Thus, the toothbrush and/or smart device may include features for determining whether the smart device is docked in the toothbrush receptacle and/or whether the smart device is removed from the receptacle. For example, a toggle switch, electrical contact, or the like, may be provided in the receptacle. When the smart device is disposed in the receptacle, the smart device contacts the switch, contact, or the like, which indicates that the smart device is docked. In some implementations, this may signal or otherwise instruct the smart device to use sensors intended for use in the retained position. Similarly, when the switch is not activated, the contact is not made, or the like, sensors may be activated that are intended for use only when the smart device is in the removed position. In other embodiments, the user may instruct one or more sensors to be active at any given time, such as by interaction with a switch or other user interface, including the interfaces 138 described below.

Although some example configurations for retaining the smart device in the toothbrush are illustrated and described herein, the disclosure is not limited to any configuration. The smart device 104 will now be described in greater detail.

Referring to FIG. 1A, the smart device 104 is illustrated as an elongated tubular structure. The smart device 104 has a housing 132 that extends between a gripping end 134 (which can be conceptually considered as the proximal end) and a sensing end 136 (which can be conceptually considered as the distal end). A boss 140 is disposed at the gripping end 134 in FIG. 1A. The boss 140 may be provided to enhance the grip, to promote retention of the smart device 104 in the toothbrush 102, and/or for a desired aesthetic.

FIG. 1A illustrates that the smart device 104 may also include a plurality of user interfaces 138 accessible to a user on an outside of the housing 132. For example, the user interfaces 138 may comprises switches, buttons, toggles, or the like. The interfaces 138 may be actuated by a user to perform a certain diagnostic task. For example, each of the user interfaces 138 may be associated with a different task. One or more of the interfaces 138 may also or alternatively control power to the smart device, allowing a user to turn the smart device on and off, for example. In still other embodiments, the smart device 104 may include a transmitter and/or receiver, such as a blue tooth, Wi-Fi, or Near Field Communication (NFC) transmitter/receiver and the user interfaces may be used to pair the smart device 104 to a separate electronic device, such as a personal device or a remote device, and/or to transmit information from the smart device 104.

Although not illustrated, some or all of the housing 132 may be covered with an outer layer, such as an elastomeric material. Suitable elastomeric materials include thermoplastic elastomers (TPE) or other similar materials used in oral care products. The elastomeric material of the outer layer may have a hardness durometer measurement ranging between A13 to A50 Shore hardness, for example, although materials outside this range may be used. A preferred range of the hardness durometer rating may be between A25 to A40 Shore hardness. An over-molding construction may be preferred for such an outer layer, a suitable deformable thermoplastic material, such as TPE, may be formed in a thin layer and attached to the sidewall 138 with an appropriate adhesive or by other means.

Figure 2:
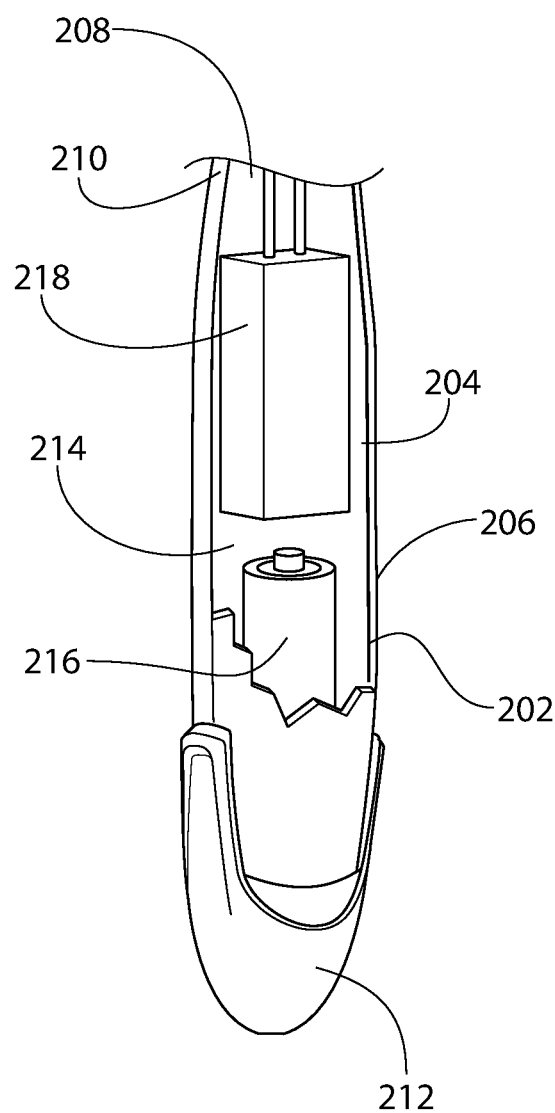
FIG. 2 is a partial perspective view of the smart device illustrated in FIG. 1A, according to example implementations of this disclosure.

As best illustrated in FIG. 2, the housing 132 comprises a contoured sidewall 202 having an inner surface 204 and an outer surface 206. In some implementations, the sidewall 202 may be constructed of a material that is sufficiently rigid to provide the necessary structural integrity for the smart device 104. For example, the sidewall can be made out of a moldable hard plastic. Moldable thermoplastics are preferred. Suitable plastics include polymers and copolymers of ethylene, propylene, butadiene, vinyl compounds and polyesters such as polyethylene terephthalate. The chosen plastic(s), however, should be compatible with agents commonly associated with oral health and the oral cavity and should not be corroded or degraded when used in and around the oral cavity.

In some implementations, the sidewall 202 may be made of a plurality of pieces that are connected after fabrication. For example, in the example illustrated in FIG. 2, the sidewall 202 includes an upper cover 208, a bottom cover 210, and a battery cover 212. In this example, the upper cover 208 and the bottom cover 210 are fixed to each other and the battery cover 212 is removably secured to an opening at the gripping end 134, to facilitate insertion and removal of a battery into and from the smart device 104, for example. In other implementations, the upper cover and the bottom cover may be formed as a unitary piece. Moreover, additional or other components may make up the sidewall 202.

Regardless of the composition, the sidewall 202 forms an internal chamber 214 in which electronic and control components of the smart device 104 are contained. As illustrated, components within the smart device 104 may include a battery 216 and electronics, generally denoted by reference numeral 218. The battery 216 may be any conventional power source, including but not limited to the illustrated dry cell battery. The power source may be disposable or rechargeable. When the power source is rechargeable, the smart device 104 may be compatible with a charger, such as a cord or dock.

The smart device 104 may be used for any or all of a number of diagnostic applications, and thus the electronic components 218 may vary. In some implementations, some or all of the electronic components 218 may be provided on or in communication with a circuit board, such as a printed circuit board or an integrated circuit. The electronic components may include, for example, one or more electronic sensors, movement capture sensors, and a transmitter, such as a Bluetooth transmitter, Wi-Fi transmitter, or the like. Some of the components may be intended to be used only when the smart device 104 is removed from the toothbrush 102, while others may be used when the smart device 104 is retained in the toothbrush 102. Several applications of the oral care system 100 will be described with reference to FIGS. 3A-7, below.

In some example embodiments, the oral care system 100 may be used to monitor toothbrushing by a user of the toothbrush 102. More specifically, in this application, the smart device 104 is retained in the toothbrush 102 while the user brushes his teeth. The electronics in the smart device include movement capture sensors, which may include one or more of a digital gyroscope and a digital accelerometer. The components may also include a digital comparator. The components also include a transmitter for relaying sensed data.

For example, as a user brushes his teeth using the toothbrush 102, the smart device 104, which is fixed relative to the toothbrush 102, senses position and/or movement of the toothbrush. Using the position and movement data, the smart device 104 may determine which teeth have been brushed. For example, changing positions of the toothbrush may be sensed and compared to a pre-determined mapping of the user's oral cavity. This sensed and compared information may also be provided to the user according to implementations of this disclosure, for example, via an electronic device.

Figure 3A:
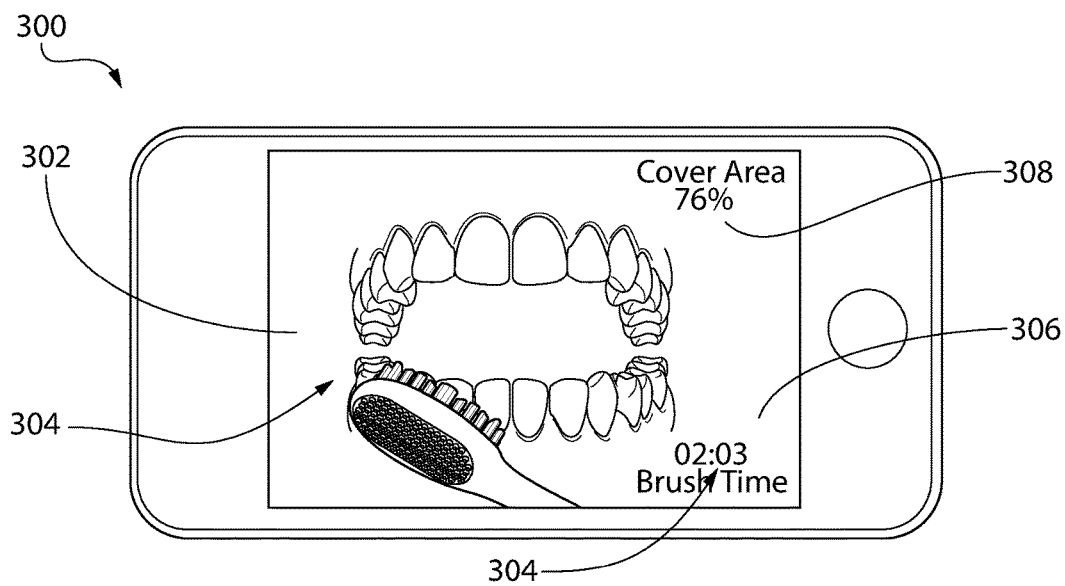
FIGS. 3A and 3B are plan views of an electronic device displaying information relating to oral care, according to an example implementation of this disclosure.
Figure 3B:
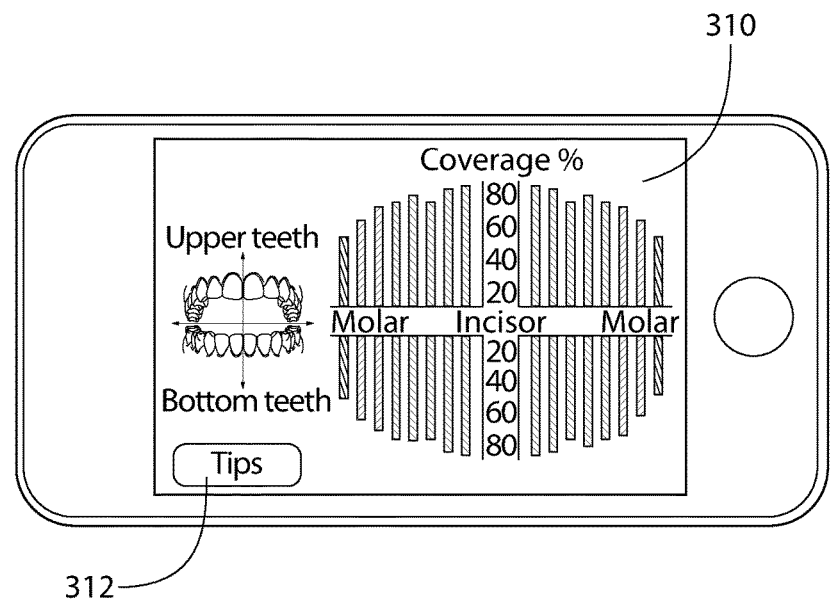

In FIGS. 3A and 3B, an electronic device 300 is embodied as a smart phone. This disclosure is not limited to the use of any specific electronic device. As illustrated in FIG. 3A, a display 302 on the electronic device displays a rendering 304 of the oral cavity and the toothbrush. In some implementations, sensors in the smart device 104 comprising the electronic components 218 sense movement of the toothbrush 102, and information about that sensed movement is transmitted to the electronic device, e.g., using a transmitter in the smart device. This information may then be used by an application running on the electronic device to graphically illustrate the concurrent toothbrushing being performed. As illustrated in FIG. 3A, the display 302 may also display additional information about the toothbrushing. For example, the display 302 may show a timer 306 or the like illustrating a duration of toothbrushing. The timer 306 may function as a stopwatch, tracking the amount of time spent brushing, or it may count down to zero, suggesting a brushing duration to the user. Moreover, as also illustrated in FIG. 3A, the display 302 may include a coverage tracker 308, which displays, as a percentage, an amount of the oral cavity or the teeth that has been brushed. Although not illustrated, the display 302 may also highlight areas that have not yet been brushed adequately, or at all. Other modifications to the display 302 also are contemplated.

In FIG. 3B, additional information about toothbrushing is provided on the display 302. In that figures, the device 300 displays a graph 310 that depicts how well each tooth was brushed. More specifically, each bar on the graph corresponds to a specific tooth, and the height of each bar conveys how well that tooth, in terms of a percentage of the surface of the tooth was brushed. With the information provided on the electronic device 300, the user can readily observe how well each tooth has been brushed. Of course, if a user realizes that he failed to brush one or more teeth sufficiently, he can perform additional brushing to ensure adequate brushing.

As should be appreciated, in the applications of the system 100 described with reference to FIGS. 3A and 3B, the smart device 104 is retained in the toothbrush 102. The smart device 104 includes the positional and/or motion sensors, which may include a gyroscope and/or an accelerometer, for example. Thus, the smart device 104 and the toothbrush 102 are intended to function together.

Figure 4A:
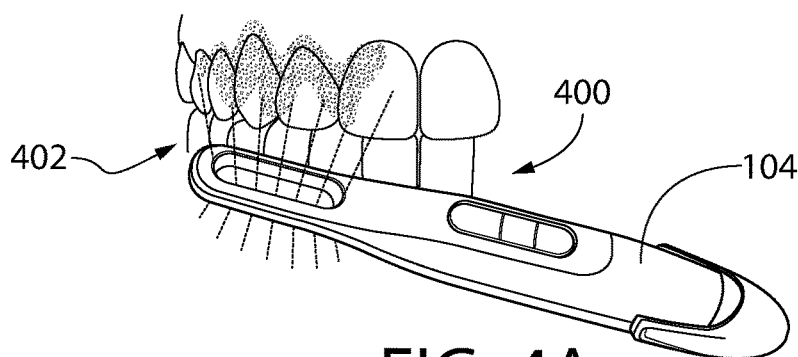
FIG. 4A is a perspective view illustrating an example of another use of a smart device such as the smart device illustrated in FIG. 2.
Figure 4B:
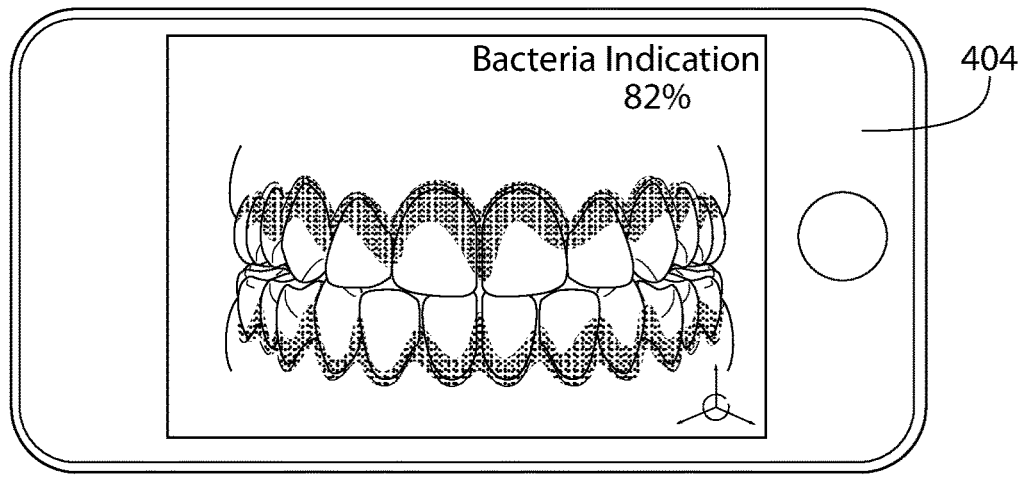
FIGS. 4B and 4C are plan views of an electronic device displaying information relating to oral care sensed during the use illustrated in FIG. 4A.
Figure 4C:
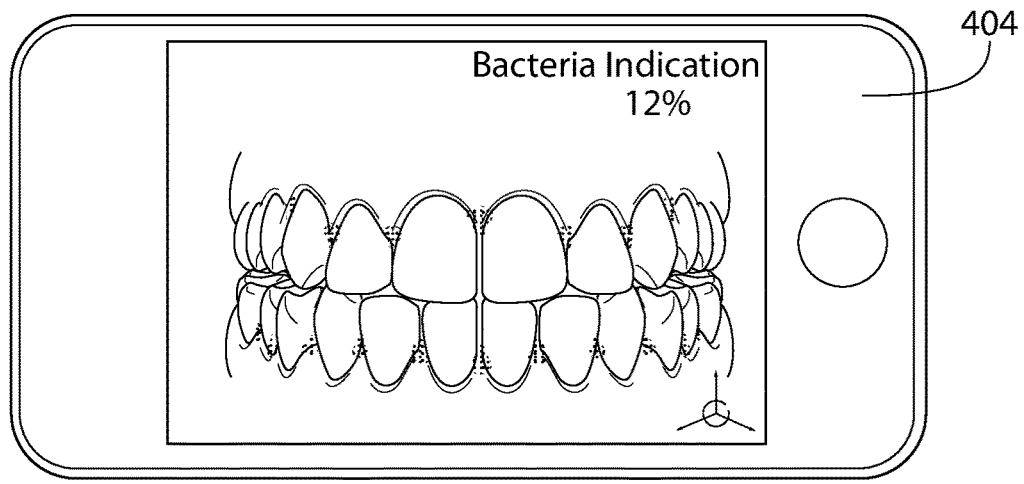

FIGS. 4A through 4C illustrate another implementation of this disclosure in which the smart device 104 is used independently of the toothbrush. For example, FIG. 4A illustrates the smart device 104 positioned proximate a user's teeth 400. In this example, the smart device 104 includes a light emitter, which emits light 402 at a frequency for illuminating bacteria in the oral cavity. A sensor also is disposed on the smart device 104 to sense the illuminated bacteria. As with the embodiment discussed above with reference to FIGS. 3A and 3B, the smart device 104 may also sense the position of the smart device relative to features of the oral cavity, and the location and amount of bacteria may be mapped to a model of the oral cavity. Information about the location, amount, or other characteristics of the bacteria may then be transmitted from the smart device 104, for display to a user on an electronic device.

FIGS. 4B and 4C show an electronic device 404, e.g., a smartphone, displaying the results of the bacteria scan on an image of the teeth. For example, FIG. 4B may illustrate results of a scan of the oral cavity before brushing, flossing, and/or rinsing and FIG. 4C may illustrate the results of a scan after brushing, flossing, and/or rinsing. In addition to depicting the bacteria on the teeth and gums in FIGS. 4B and 4C, the electronic device may also display other metrics of cleanliness of the teeth and gums. For example, a bacteria counter 406 may be provided, which, in the implementations illustrated in the figures, indicates a percentage of bacterial coverage on the teeth and gums. In other implementations, the bacteria counter 406 may instead give a number of identified bacteria.

Figure 5A:
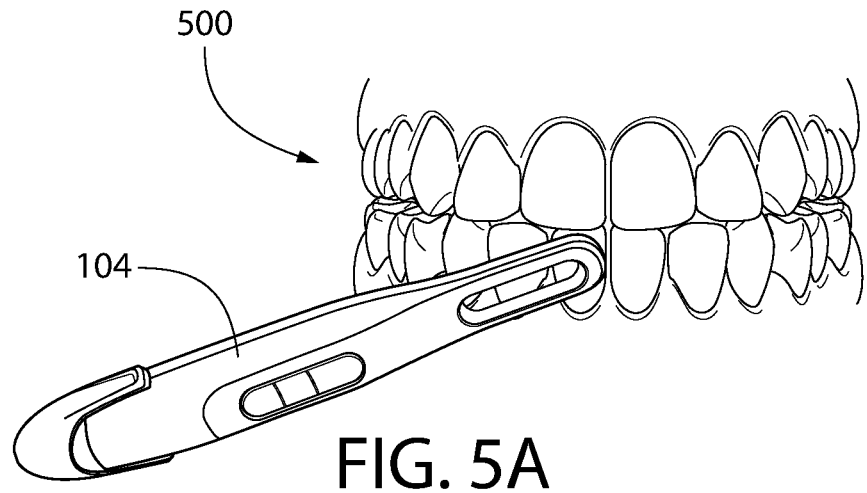
FIG. 5A is a perspective view illustrating an example use of a smart device, such as the smart device illustrated in FIG. 2, according to example implementations of this disclosure.
Figure 5B:
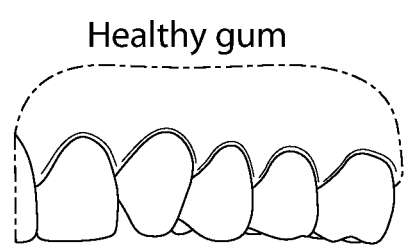
FIGS. 5B-5D are illustrations of different oral care conditions sensed during the use illustrated in FIG. 5A.
Figure 5C:
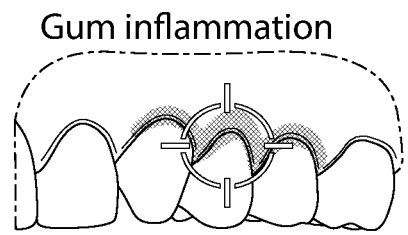
Figure 5D:
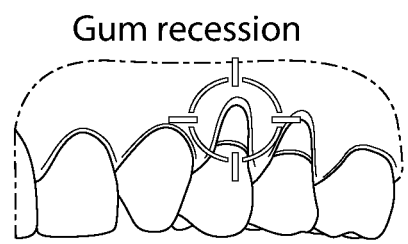

FIGS. 5A through 5D illustrate another example use of the smart device 104, detached from the toothbrush 102. In these embodiments, the smart device 104 is used to diagnose gum maladies. More specifically, FIG. 5A illustrates that, as in the embodiment of FIG. 4A, the user passes the smart device 104 near the teeth and gums 500 to sense conditions. Located at the sensing end 136 of the smart device 104 may be a camera or other image capturing member, which acquires images of the teeth and gums. The images may then be transferred to the user device, such as an electronic device, and displayed for viewing by the user. FIG. 5B illustrates a healthy gum, FIG. 5C shows gum inflammation, and FIG. 5D shows gum recession. The display on the user device may indicate any or all detected gum conditions, including but not limited to inflammation and/or recession, as well as bleeding, gingivitis, periodontal disease, or the like. The images captured by the sensing device 100 may be compared to "healthy" oral features to determine abnormalities, for example. Moreover, the electronic device may display steps the user should take to treat any maladies discovered.

Figure 6:
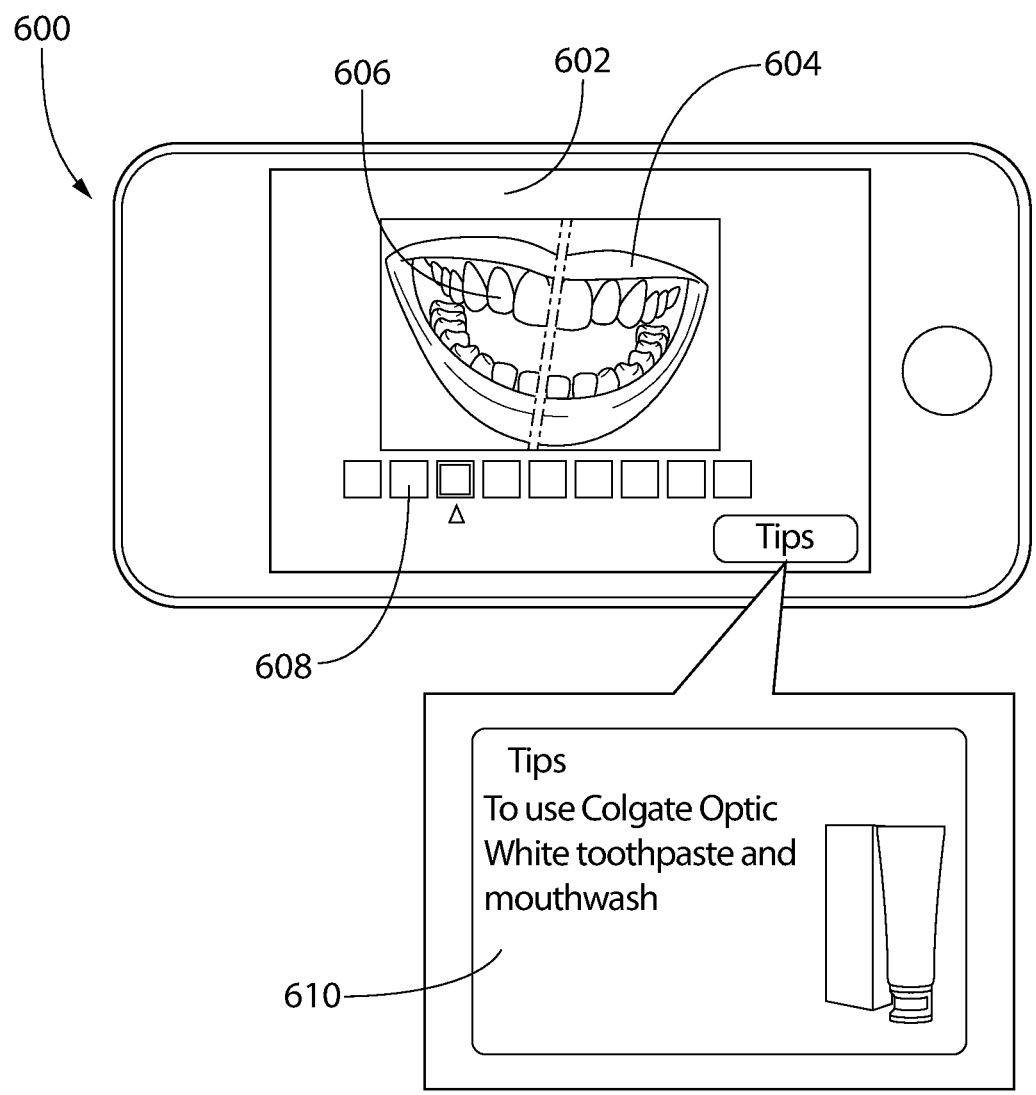
FIG. 6 is a plan view of an electronic device displaying information relating to oral care sensed by a smart device, such as the smart device illustrated in FIG. 2, according to other example implementations of this disclosure.

FIG. 6 illustrates another use case for the smart device 104. In this embodiment, the smart device may include an image capture device at the sensing end 136 that takes color images of the user's teeth. The smart device may also include a transmitter, as in embodiments described above, and transmit the captured images to an electronic device 600.

In this example, the color images may be used to evaluate tooth whiteness. For example, information from the captured images may be used to determine a color of the user's teeth. A display 602 of the electronic device 600 may then display an image of the user's teeth, with a color representing the color of the user's teeth, such as at 604. The display 602 may also illustrate a historical image 606 of the user's teeth, for example, so the user can determine how well a whitening regimen is working. In addition, or alternatively, the display 602 may also present to the user a color scale 608, including an array of tooth colors and against which the user may compare her teeth.

Figure 7A:
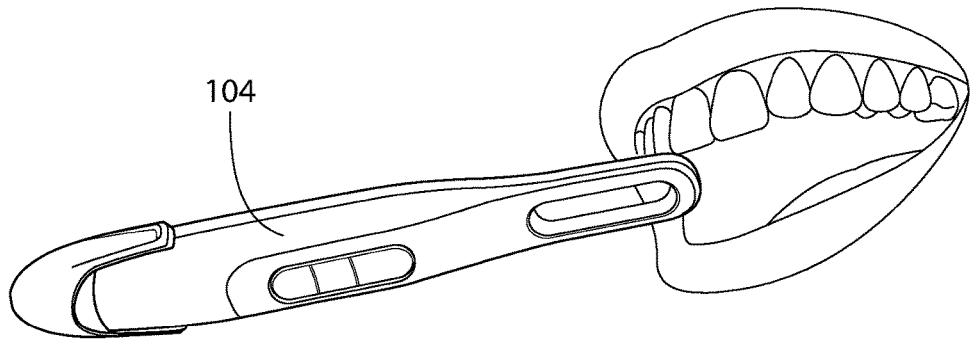
FIG. 7A is a perspective view illustrating another example use of a smart device, such as the smart device illustrated in FIG. 2, according to example implementations of this disclosure.
Figure 7B:
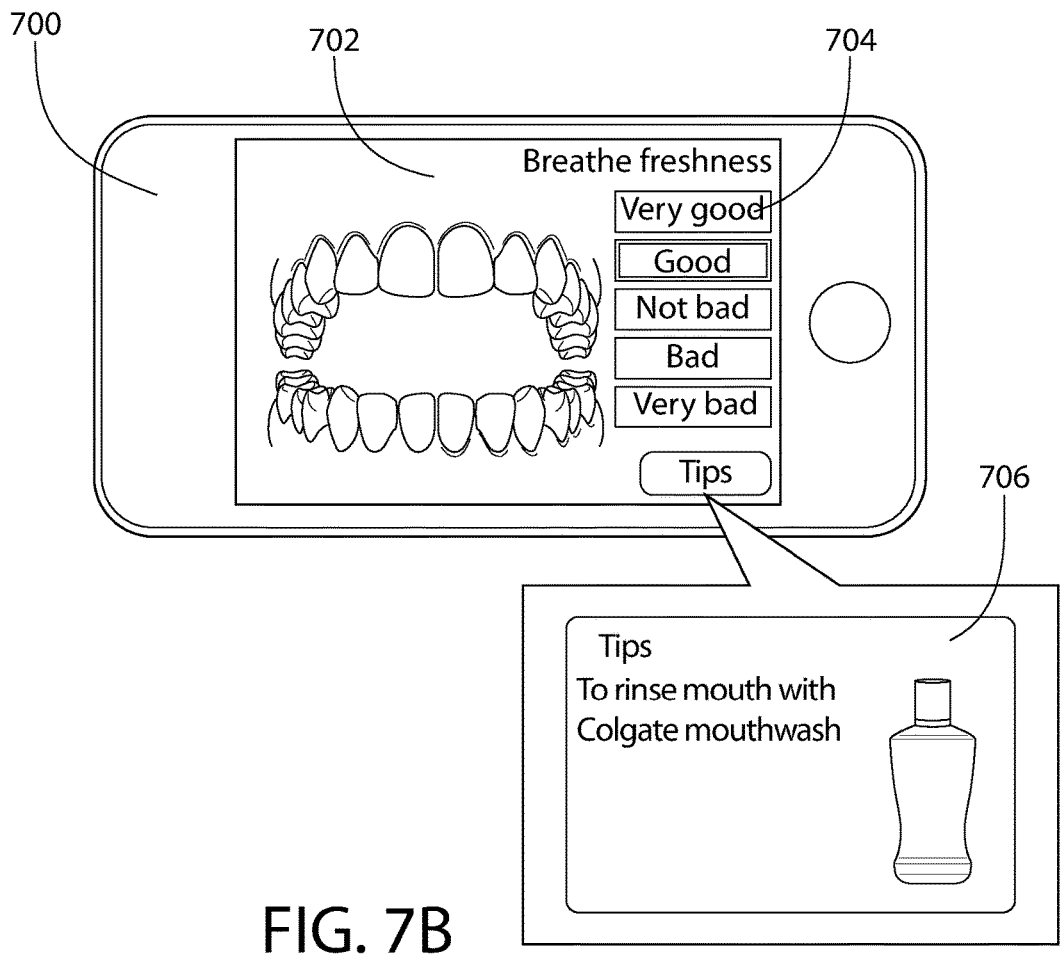
FIG. 7B is a plan view of an electronic device displaying information relating to oral care sensed during the use illustrated in FIG. 7A.

FIGS. 7A and 7B illustrate another example use of the smart device 104, separate from the toothbrush 102. In this example, the smart device 104 includes a breath freshness sensor at the sensing end 136. When a user breaths on the sensing end 136, the sensor will collect data useful to determine breath freshness. For example, a level of sulfur or some malodorous compound may be detected by the sensor. Information about the sulfur level may then be transmitted to a user device, such as an electronic device 700. A display 702 on the user device may then display information about the user's breath. For example, the display 702 may include a breath freshness gauge 704 that rates the user's breath on a scale from very bad to very good. For example, an application running on the electronic device 700 may compare the amount of detected sulfur to a predetermined scale that associates an amount of sulfur to a breath freshness, e.g., very good, bad, very bad, etc. Other scales or displays for conveying the information may also be used without departing from the spirit and scope of this disclosure.

As should be appreciated from the foregoing, implementations of this disclosure provide an oral care system 100 including a toothbrush 102 and a smart device releasably retained in the toothbrush 102. The smart device 104 incorporates sensors and other components that collect information relating to oral health. The smart device is used to capture some information while the smart device is retained in the toothbrush, and other information independent of the toothbrush 102. In this manner, the smart device 104 provides a diagnostic tool useful in both retained and separated positions, relative to the toothbrush 102. In each of the embodiments described above, information sensed, measured or otherwise obtained by the smart device 104 is then transferred to an electronic device. Although a smartphone or other personal device is illustrated, in other examples, information may be sent to an oral care provider, such as a dentist or orthodontist. For example, the oral care provider may be able to prescribe some course of action to counter a malady detected by the smart device 104. The oral care provider may also be able to track the brushing habits of the user, and thus correct incorrect habits.

Examples user displays were illustrated in connection with embodiments describe above, but this disclosure is not limited to those displays. One or more applications may be developed to further inform and educate the user. For example, in several of displays illustrated, a button, icon, or other user interaction section is labeled "Tips." In some implementations, the user may interact with the application running on the device by touching the "Tips" icon, and the application presents additional information to the user. Such an icon 312 is illustrated in FIG. 3, for example. The user may activate the icon to be provided with additional information about effective toothbrushing. The additional information may be displayed as a separate page or as an overlaying window. In other embodiments, selecting the "Tips" icon 312 may redirect the user to another page or resource. For example, the "Tips" icon may facilitate creation of a query to an oral health care provider.

FIG. 6 includes an example of a "tips" pop-up screen, window, or other visual representation 610 that may be provided on the display 602 to provide the user with additional information relative to teeth whitening. More specifically, the representation 610 may instruct the user on products to use to enhance whitening. A similar "tips" screen 706 is illustrated in FIG. 7B. The screen 706 provides the user with additional instruction for freshening her breath. Other, similar information may be accessible in a similar manner in other use cases.

The smart device 104 may be releasably retained in the toothbrush 102 in any of a number of ways. For example, detents, interference fits, threaded engagements and the like may be employed. In one example embodiment, an annular groove may be formed in the outside surface of the housing of the smart device. A complementary annular protrusion may be formed on an inner surface of the cavity in the handle, in which the smart device is retained. When the smart device is sufficiently inserted into the cavity, the annular groove slides to a position in which the annular protrusion is disposed therein. When a sufficient force is applied on the smart device, the annular protrusion is unseated from in the annular groove.

Modifications to the system 100 may also be made. For example, the smart device may also contain a reservoir 308 for holding an oral care material or product, which can be any active or inactive oral care agent. The oral care agent and/or its carrier may be in any form such as a solid or a flowable material including without limitation viscous pastes/gels or less viscous liquid compositions. Preferably, the oral care agent is a flowable material in preferred embodiments. Any suitable oral care agent can be used in the present invention. For example, the oral care agent includes whitening agents, including without limitation, peroxide containing tooth whitening compositions. Contemplated oral care agents can be an active or non-active ingredient, including without limitation, antibacterial agents; oxidative or whitening agents; enamel strengthening or repair agents; tooth erosion preventing agents; anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents; anti-inflammatory agents; dry mouth relief ingredients; catalysts to enhance the activity of any of these agents; colorants or aesthetic ingredients; and combinations thereof. The oral care agent in one embodiment is preferably free of (i.e., is not) toothpaste. Instead, the active agent is intended to provide supplemental oral care benefits in addition to merely brushing one's teeth. Other suitable oral care agents could include lip balm or other materials that are typically available in a semi-solid state.

Although example embodiments have been described in language specific to the structural features and/or methodological acts, the claims are not necessarily limited to the specific features or acts described. Rather, the specific features and acts are disclosed as illustrative forms of implementing the example embodiments.

What is claimed is:
1. An oral care system comprising:
a handle extending from a proximal end to a distal end, the handle comprising a sidewall defining a receptacle in the handle and an opening to the receptacle at the proximal end of the handle;
a head disposed proximate the distal end of the handle and comprising a tooth cleaning element; and
a smart device selectively receivable in the receptacle of the handle and comprising a first sensor for acquiring first oral health data with the smart device in a retained position in the receptacle in the handle and a second sensor for acquiring second oral health data with the smart device in a removed position, separate from the handle.

2. The oral care system of claim 1, wherein the first sensor comprises a sensor for determining a position or orientation of the handle or the head with the smart device in the retained position.

3. The oral care system of claim 2, wherein the smart device further comprises a transmitter for transmitting information relating to the position or orientation to a receiver separate from a toothbrush comprising the handle and the head.

4. The oral care system of claim 3, wherein the receiver separate from the toothbrush is associated with an electronic device.

5. The oral care system of claim 4, wherein the electronic device is configured to run an oral health application that displays to a user information about the user's oral health.

6. The oral care system of claim 1, wherein the second sensor comprises an imaging sensor.

7. The oral care system of claim 6, wherein the imaging sensor captures an image of at least a portion of an oral cavity.

8. The oral care system of claim 6, wherein the imaging sensor captures a color image of at least a portion of an oral cavity.

9. The oral care system of claim 1, wherein the smart device further comprises a light emitter for illuminating a portion of an oral cavity.

10. The oral care system of claim 1, wherein the second sensor monitors breath freshness.

11. The oral care system of claim 10, wherein the second sensor measures a sulfur level in the breath to determine breath freshness.

12. The oral care system of claim 1, wherein the smart device comprises at least one of a digital gyroscope, a digital accelerometer, and a digital comparator.

13. The oral care system of claim 1, wherein the smart device comprises a transmitter and a power source.

14. A method of measuring an oral health condition using a toothbrush, the toothbrush comprising a handle having a sidewall defining a receptacle, a head disposed proximate a distal end of the handle and including a tooth cleaning element, and a smart device removably disposed in the receptacle in the handle, the smart device including a first sensor for sensing a position or a movement of the toothbrush and a second sensor for sensing a parameter associated with the oral health condition, the method comprising:

sensing at least one of a position or a movement of the toothbrush, by the first sensor of the smart device, with the smart device retained in the receptacle in the handle;

sensing the parameter associated with the oral health condition, by the second sensor of the smart device, with the smart device removed from the receptacle in the handle and placed in a sensing position proximate an oral cavity; and transmitting the position or the movement of the toothbrush or the parameter associated with the oral health condition.

15. The method of claim 14, wherein the parameter associated with the oral health condition is displayed on an electronic device.

16. The method of claim 15, wherein a visual representation containing information relative to the parameter associated with the oral health condition is displayed with the parameter associated with the oral health condition on the electronic device.

17. The method of claim 15, wherein the electronic device is a personal electronic device associated with the user.

18. The method of claim 14, wherein the transmitting the parameter associated with the oral health condition comprises transmitting the parameter to an oral health care provider.

19. The method of claims 14, wherein the parameter associated with the oral health condition is tooth color and further comprising displaying a color image captured by the smart device to the user together with a reference image.

20. The method of claim 19, wherein the reference image comprises at least one of an historical image of the user's teeth, or a color scale.

* * * * *